United States Patent [19]
Nadeau et al.

[11] Patent Number: 5,846,726
[45] Date of Patent: Dec. 8, 1998

[54] DETECTION OF NUCLEIC ACIDS BY FLUORESCENCE QUENCHING

[75] Inventors: James G. Nadeau, Chapel Hill; J. Bruce Pitner, Durham; James L. Schram, Knightdale; C. Preston Linn, Durham; Glenn P. Vonk, Fuquay-Varina; G. Terrance Walker, Chapel Hill, all of N.C.

[73] Assignee: Becton, Dickinson and Company, Franklin Lakes, N.J.

[21] Appl. No.: 855,085

[22] Filed: May 13, 1997

[51] Int. Cl.$^6$ .............. C12Q 1/68; C07H 21/04; C12P 19/34
[52] U.S. Cl. .............. 435/6; 435/91.2; 536/24.3; 536/25.3; 536/25.32
[58] Field of Search .............. 435/6, 91.2; 536/24.3, 536/24.33, 25.3, 25.32

[56] References Cited

U.S. PATENT DOCUMENTS

| | | | |
|---|---|---|---|
| 5,538,848 | 7/1996 | Livak et al. | 435/5 |
| 5,547,861 | 8/1996 | Nadeau et al. | 435/91.2 |
| 5,550,025 | 8/1996 | Walker | 435/6 |
| 5,593,867 | 1/1997 | Walker et al. | 435/91.2 |

FOREIGN PATENT DOCUMENTS

| | | |
|---|---|---|
| 93015439 B | 3/1993 | Japan . |
| WO 96/21144 | 7/1996 | WIPO . |

OTHER PUBLICATIONS

L. G. Lee, et al. "Allelic discrimination by nick–translation PCR with fluorogenic probes" *Nucl. Acids Res.* 21:3761–3766 (1993).

S. P. Lee, et al. "Fluorometric Assay for DNA Cleavage Reactions Characterized with BamHI Restriction Endonuclease" *Anal. Biochem.* 220:377–383 (1994).

S. S. Ghosh, et al. "Real time kinetics of restriction endonuclease cleavage monitored by fluorescence resonance energy transfer" *Nucl. Acids Res.* 22:3155–3159 (1994).

Zhu et al. Nucleic Acids Research. 1994. vol. 24. No. 16. pp. 3418–3422.

S.S. Ghosh, et al. Real time kinetics of restriction endonuclease cleavage monitored by fluorescene resonance energy transfer, Nucl. Acids Res. 22: 3155–3159 (1994).

*Primary Examiner*—John L. LeGuyader
*Assistant Examiner*—Mark L. Shibuya
*Attorney, Agent, or Firm*—Donna R. Fugit

[57] ABSTRACT

Single-stranded signal primers are modified by linkage to two dyes which form a donor/acceptor dye pair. The two dyes are positioned in sufficiently close spatial proximity on the signal primer that the fluorescence of the first dye is quenched by the second dye. The signal primer may further comprise a restriction endonuclease recognition site (RERS) between the two dyes. As the signal primer is initially single-stranded and remains single-stranded in the absence of target, the restriction endonuclease recognition site is not cleavable or nickable by the restriction endonuclease. In the presence of target, however, signal primer and the restriction endonuclease recognition site are rendered double-stranded and cleavable or nickable by the restriction endonuclease. Cleavage or nicking separates the two dyes and a change in fluorescence due to decreased quenching is detected as an indication of the presence of the target sequence or of target sequence amplification.

51 Claims, 3 Drawing Sheets

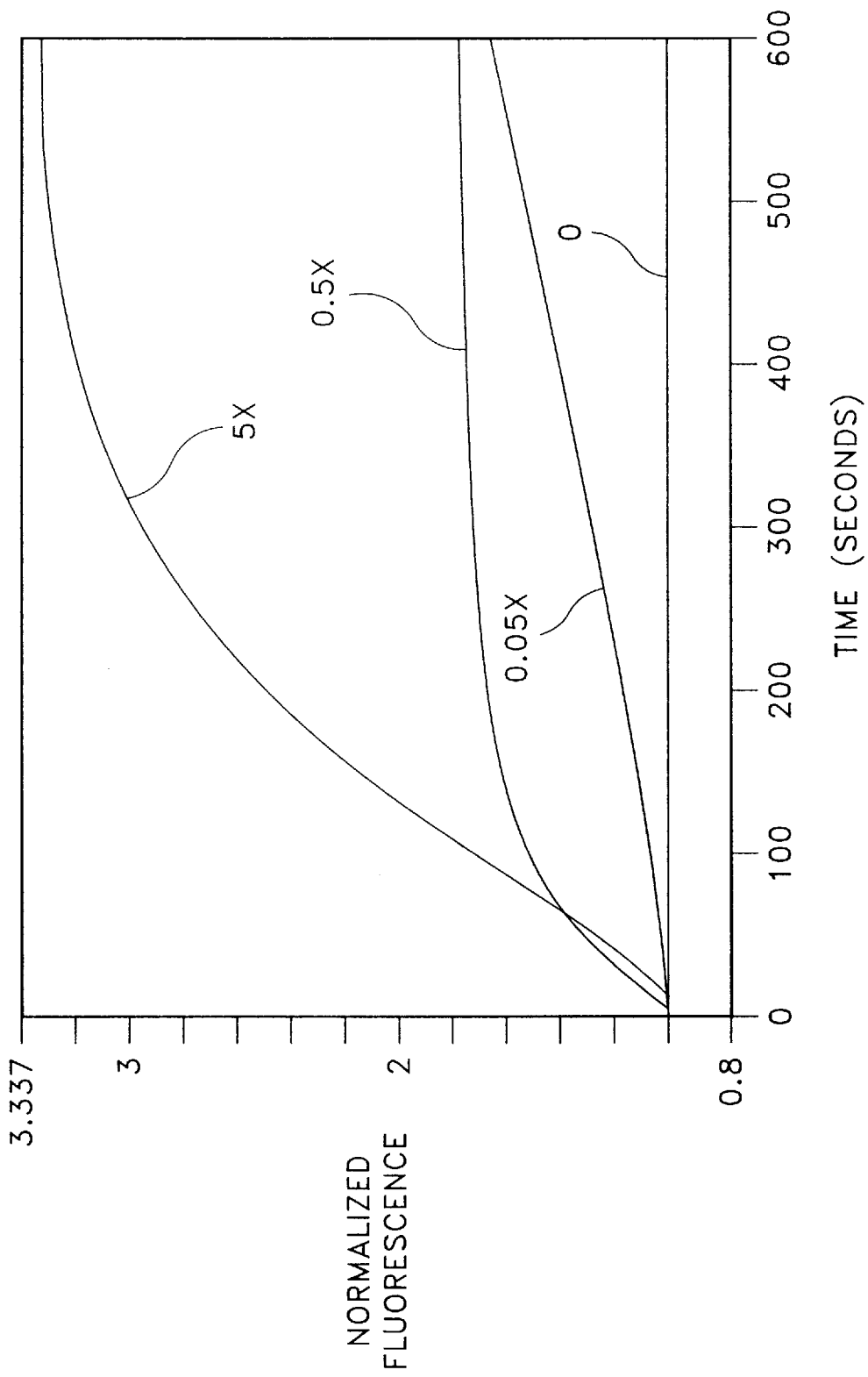

DETECTION OF NUCLEIC ACIDS BY FLUORESCENCE QUENCHING

FIELD OF THE INVENTION

The invention relates to methods for detecting nucleic acid target sequences, and in particular to detection methods employing fluorescence quenching.

BACKGROUND OF THE INVENTION

Sequence-specific hybridization of oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) for detection of probe hybridization rather than direct detection of fluorescence intensity. Fluorescence energy transfer occurs between a donor fluorophore and an acceptor dye (which may or may not be a fluorophore) when the absorption spectrum of one (the acceptor) overlaps the emission spectrum of the other (the donor) and the two dyes are in close proximity. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Forster (1948. Ann. Phys. 2, 55–75). The distance between donor and acceptor dyes at which energy transfer efficiency is 50% is referred to as the Forster distance ($R_o$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogenous assays generally require additional steps to separate hybridized label from free label. Typically, FET and related methods have relied upon monitoring a change in the fluorecence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the acceptor. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352). Alternatively, the donor and acceptor may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, a self-complementary oligonucleotide labeled at each end may form a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. A "double imperfect hairpin" scheme is described by B. Bagwell, et al. (1994. *Nucl. Acids Res.* 22, 2424–2425; U.S. Pat. No. 5,607,834). Kramer and Tyagi (1996. *Nature Biotech.* 14, 303–308) describe a hairpin with the detector sequence in a loop between the arms of the hairpin.

Homogeneous methods employing energy transfer or fluorescence quenching for detection of nucleic acid amplification have also been described. R. Higuchi, et al. (1992. *Biotechnology* 10, 413–417) disclose methods for detecting DNA amplification in real-time by monitoring increased fluorescence for ethidium bromide as it binds to double-stranded DNA. The sensitivity of this method is limited because binding of the ethidium bromide is not target specific and background amplification products are also detected. L. G. Lee, et al. (1993. *Nuc. Acids Res.* 21, 3761–3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, spearating two fluorescent dyes which form an energy transfer pair. Fluorescence intensity increases as the probe is digested. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target. There is no specific disclosure of how a restriction endonuclease would be used in a fluorescence energy transfer system.

Energy transfer and fluorescence quenching detection methods have also been applied to detecting a target sequence by hybridization of a specific probe. Japanese Patent No. 93015439 B discloses methods for measuring polynucleotides by hybridizing the single-stranded target to a single-stranded polynucleotide probe tagged with two labels which form an energy transfer pair. The double-stranded hybrid is cleaved by a restriction enzyme between the labels and fluorescence of one of the labels is measured. A shortcoming of this method is that the restriction site in the probe must also be present in the target sequence being detected. The patent does not describe adaptation of the probe for use in assays where the target sequence does not contain an appropriate restriction site or where cleavage of the target is not desired. S. S. Ghosh, et al. (1994. *Nucl. Acids Res.* 22, 3155–3159) describe restriction enzyme catalyzed cleavage reactions of fluorophore-labeled oligonucleotides which are analyzed using fluorescence resonance energy transfer. In these assays, the complementary oligonucleotides are hybridized (not amplified) to produce the double-stranded restriction site, and one of the fluorescent labels is linked to each of the two strands (i.e., they are not linked to the same strand, see FIG. 1 of Ghosh, et al.). S. P. Lee, et al. (1994. *Anal. Biochem.* 220, 377–383) describe fluorescence "dequenching" techniques using restriction endonucleases to cleave double-stranded DNA. However, these methods relate to assays employing only a single fluorescent label which is quenched by interaction with the DNA, not by fluorescence energy transfer from a second fluorescent label. The observed quenching effect may therefore be sequence-specific and not generally applicable. Hybridization of the labeled oligonucleotide to its complement and cleavage of the double-stranded restriction site relieved non-transfer quenching of the label and quenched fluorescence was totally recovered.

Signal primers (sometimes referred to as detector probes) which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins. Examples of detection methods for use with signal primers are described in U.S. Pat. No. 5,550,025 (incorporation of lipophilic dyes and restriction sites) and U.S. Pat. No. 5,593,867 (fluorescence polarization detection).

SUMMARY OF THE INVENTION

The present invention employs hybridization and extension of a signal primer for detection of nucleic acid target sequences by fluorescence quenching mechanisms. The single-stranded signal primer is modified by linkage to two dyes which form an energy transfer pair. The two dyes are positioned in proximity to each other on the signal primer such that the fluorescence of the first dye is quenched by the second dye. The signal primer may further comprise a restriction endonuclease recognition site (RERS) between the two dyes. As the signal primer is initially single-stranded and remains single-stranded in the absence of target, the restriction endonuclease recognition site is not cleavable by the restriction endonuclease. As a result of target-dependent synthesis of a complementary strand, however, the signal primer and its RERS are rendered double-stranded, making the RERS cleavable or nickable by the restriction endonuclease. Cleavage separates the two dyes and the fluorescence intensity of the first dye increases (i.e., quenching is decreased) as an indication of the presence of the target sequence. A decrease in the fluorescence intensity of the second dye upon cleavage or nicking may also be detectable.

In a first embodiment, the signal primer of the invention is employed in an amplification reaction for detection of target sequence amplification. In an alternative embodiment for non-amplification based detection of target sequences, the signal primer is hybridized at the 3' end of the target oligonucleotide such that the restriction endonuclease recognition site forms a 5' overhang. Extension of the target sequence on the signal primer using polymerase produces a fully double-stranded restriction site which is cleaved or nicked to separate the dyes. This results in a change in fluorescence which indicates the presence of the target sequence.

DESCRIPTION OF THE DRAWINGS

FIG. 3 shows the change in fluorescence intensity associated with hybridization, extension and cleavage of a signal primer according to the invention.

DETAILED DESCRIPTION OF THE INVENTION

Figure 1:
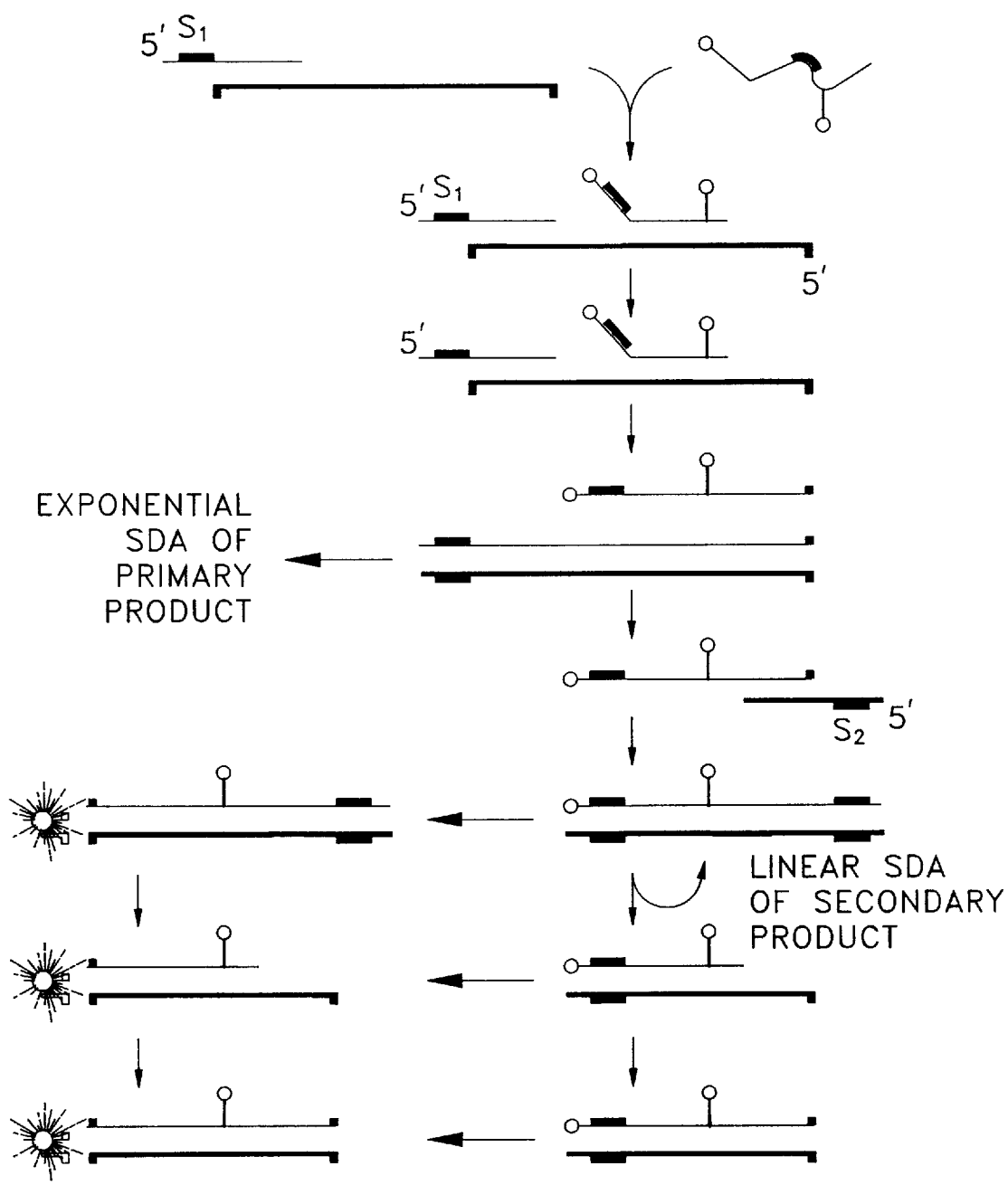
FIG. 1 illustrates the signal primer reaction scheme for use in detection of target amplification according to the invention.

The present invention employs signal primers in hybridization and extension reactions to produce double-stranded products which contain a donor/acceptor dye pair. Fluorescence quenching occurs in the signal primer. Conversion of the single-stranded signal primer to double-stranded form also converts a single-stranded restriction endonuclease cleavage site in the signal primer to double-stranded form, rendering it cleavable or nickable by the restriction endonuclease. Cleavage or nicking by the restriction endonuclease separates the donor and acceptor dyes, resulting in decreased quenching of donor fluorescence and an increase in donor fluorescence intensity. An associated change in a fluorescence parameter (e.g., an increase in donor fluorescence intensity, a decrease in acceptor fluorescence intensity or the ratio of the two) is monitored as a indication of target sequence amplification. Monitoring of the change in donor fluorescence is preferred, as this change is typically larger than the change in acceptor fluorescence. Other fluorescence parameters such as a change in fluorescence lifetime may also be monitored.

Terms relating to nucleic acid target amplification and signal primers are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is hemimodified ("nicking"), as described in U.S. Pat. No. 5,455,166; U.S. Pat. No. 5,270,184 and; EP 0 684 315. A hemimodified recognition site is a double stranded recognition site for a restriction endonuclease in which one strand contains at least one derivatized nucleotide which causes the restriction endonuclease to nick the primer strand rather than cleave both strands of the recognition site. Usually, the primer strand of the hemimodified recognition site does not contain derivatized nucleotides and is nicked by the restriction endonuclease. Alternatively, the primer may contain derivatized nucleotides which cause the unmodified target strand to be protected from cleavage while the modified primer strand is nicked. Such restriction endonucleases can be identified in routine screening systems in which a derivatized dNTP is incorporated into a restriction endonuclease recognition site for the enzyme. Preferred hemimodified recognition sites are hemiphosphorothioated recognition sites for the restriction endonucleases HincII, BsoBI and BsrI. The amplification primer also comprises a 3'-OH group which is extendable by DNA polymerase when the target binding sequence of the amplification primer is hybridized to the target sequence. For the majority of the SDA reaction, the amplification primer is responsible for exponential amplification of the target sequence.

As no special sequences or structures are required to drive the amplification reaction, amplification primers for PCR generally consist only of target binding sequences. Amplification primers for 3SR and NASBA, in contrast, comprise an RNA polymerase promoter near the 5' end. The promoter is appended to the target sequence and serves to drive the amplification reaction by directing transcription of multiple RNA copies of the target.

Extension products are nucleic acids which comprise a primer or a portion of a primer and a newly synthesized strand which is the complement of the target sequence downstream of the primer binding site. Extension products result from hybridization of a primer to a target sequence and extension of the primer by polymerase using the target sequence as a template.

A bumper primer is a primer which anneals to a target sequence upstream of the amplification primer, such that extension of the bumper primer displaces the downstream amplification primer and its extension product. Extension of bumper primers is one method for displacing the extension products of amplification primers, but heating is also suitable.

The terms target or target sequence refer to nucleic acid sequences to be amplified or detected. These include the original nucleic acid sequence to be amplified, its complementary second strand and either strand of a copy of the original sequence which is produced by replication or amplification. The target sequence may also be referred to as a template for extension of hybridized primers.

A signal primer comprises, at its 3' end, a target binding sequence which hybridizes to the target sequence and, 5' to the target binding sequence, a label, detectable structure or specialized sequence for detection. The signal primers of the invention comprise a restriction endonuclease recognition site in a tail portion 5' to the target binding sequence and a donor/acceptor dye pair flanking the restriction endonuclease recognition site to facilitate detection of double-stranded products generated from the signal primer. The signal primer may hybridize to a target sequence downstream of an amplification primer such that extension of the amplification primer displaces the signal primer, a portion of the signal primer or the signal primer extension product. It is then rendered double-stranded by hybridization and extension of a second amplification primer. Alternatively, for purposes of the present invention, the target binding sequence of the signal primer may hybridize at the 3' end of the target sequence forming an 5' overhang such that extension of the target on the signal primer renders the signal primer, including the restriction endonuclease recognition site, double stranded.

Amplification products, amplified products or amplicons are copies of the target sequence generated by hybridization and extension of an amplification primer. This term refers to both single stranded and double stranded amplification primer extension products which contain a copy of the original target sequence, including intermediates of the amplification reaction.

Secondary amplification products or secondary products are oligonucleotides generated from a signal primer in a target amplification-dependent manner. These terms refer to single stranded or double stranded products generated from signal primers, as well as portions of signal primers or signal primer extension products generated as a result of target amplification.

Cleavage of an oligonucleotide refers to breaking the phosphodiester bonds of both strands of a DNA duplex or breaking the bond of single-stranded DNA. This is in contrast to nicking, which refers to breaking the phosphodiester bond of only one of the two strands in a DNA duplex.

Generation of double-stranded secondary amplification products using a signal primer is illustrated in FIG. 1 and may be summarized as follows. A signal primer hybridizes to one strand of the target sequence downstream of an amplification primer. Both the amplification primer and the signal primer are extended by DNA polymerase using the target sequence as a template. The signal primer extension product is displaced from the template by extension of the upstream amplification primer and in turn serves as a template for hybridization and extension of a second amplification primer, rendering the signal primer extension product double-stranded. The RERS thereby becomes a substrate for the restriction endonuclease. A second signal primer which hybridizes to the second, complementary strand of a double stranded target sequence without overlapping the the hybridization site of the first signal primer may optionally be included in the reaction. The second signal primer hybridizes to the second strand of the target sequence downstream of the second amplification primer and is extended and displaced by extension of the second amplification primer. The second signal primer extension product is rendered double stranded by hybridization and extension of the first amplification primer. Multiple signal primers per strand of target may be employed if desired, each hybridizing to the target sequence downstream of the other on the same strand, and all signal primers being hybridized downstream of the amplification primer. In this manner, each signal primer is displaced by extension of the upstream signal primer and the most 5' signal primer is displaced by the amplification primer. Use of multiple signal primers has the advantage of increasing or amplifying the signal generated per target, with an increase in sensitivity of the assay. In SDA and other amplification reactions in which the specialized sequences or structures are required in the amplification primers, signal primers do not serve as amplification primers. Secondary amplification products are therefore either unamplifiable or not exponentially amplifiable and have the advantage of not contributing significantly to background.

The signal primers of the invention comprise a donor/acceptor dye pair linked at positions flanking a restriction endonuclease recognition site (RERS). In the single-stranded signal primer, the RERS sequence corresponds to one strand of the double-stranded RERS. The signal primer restriction endonuclease recognition site is positioned 5' to the target binding region of the signal primer so as not to interfere with hybridization of the signal primer to the target sequence or its extension by polymerase. Either the donor or acceptor dye is linked to the signal primer 3' to the RERS but preferably not at the 3' terminus of the signal primer as a 3' terminal label may interfere with hybridization and/or extension of the primer. However, if a selected donor fluorophore or acceptor dye does not inhibit hybridization and/or extension it may be linked at the 3' terminus of the signal primer. The donor fluorophore (if the acceptor is 3' to the RERS) or the acceptor (if the donor is 3' to the RERS) is linked to the signal primer at a position 5' to the RERS. That is, the donor and acceptor dyes are linked to the single-stranded signal primer such that they flank the RERS. The dyes are preferably linked on either side of the RERS at positions sufficiently close together that fluorescence quenching occurs but also sufficiently far apart to allow the restriction endonuclease access to the RERS for cleavage or nicking.

In SDA reactions, the signal primer RERS may be a sequence which is recognized by the same restriction enzyme as provides the nicking function central to SDA. That is, two different recognition sequences for the same restriction endonuclease may be employed—one in the signal primer and one in the amplification primer. In this embodiment, the sequence of the signal primer RERS may be selected such that double-stranded cleavage is not prevented when the modified deoxynucleoside triphosphates (dNTPs) of SDA are incorporated. In contrast, the sequence of the amplification primer RERS is selected such that nicking by the restriction endonuclease is induced by incorporation of modified dNTPs. For example, the CTCGAG and CCCGAG recognition sites for BsoBI remain cleavable when hemimodified, whereas the CTCGGG recognition site for the same enzyme is nicked when hemimodified. Alternatively, a recognition site for a restriction endonuclease different from that which provides the nicking function in the SDA reaction may be present in the signal primer. Again, however, the RERS in the signal primer is preferably selected such that double-stranded cleavage is not compromised by incorporation of modified dNTPs. In still another alternative embodiment, the RERS in the signal primer is selected so as to be nicked once by the restriction endonuclease, regenerating an RERS which is not renickable upon repair by the polymerase and incorporation of the modified dNTP. Such "singly-nickable" sites may be recognized by either the same restriction endonuclease which provides the nicking function in the SDA reaction or by a different restriction endonuclease. Singly nickable sites are generally canonical and contain a nucleotide at the nicking site which is the same as the modified dNTP in the SDA reaction. For example, the CCCGGG recognition site for BsoBI is nicked between the first and second C's. When used as a signal primer in an SDA reaction employing dCTPα S, repair of the nick and displacement of the strand downstream of the nick incorporates the modified C nucleotide at the nicking site. Modification of the nicking site inhibits renicking, but the initial nick separates the donor and acceptor dyes by allowing strand displacement of the downstream fragment carrying one of the dyes. Singly nickable sites are desirable in the invention because they prevent amplification of the secondary amplification product independently of amplification of the target sequence, lowering background and improving quantitation.

The signal primer is included in a nucleic acid target amplification reaction generally as described in U.S. Pat. No. 5,547,861. When added to the amplification reaction, the signal primers of the invention are converted to double-stranded form as previously described, converting the RERS to a double-stranded form which is cleavable by the restriction endonuclease. This process is illustrated in FIG. 1. "Cleavage" as used herein refers to cutting of both strands of a nucleic acid duplex by a restriction endonuclease, in contrast to "nicking" which refers to cutting of only one of the two strands in a duplex nucleic acid. Cleavage of the RERS produces two fragments of the double-stranded secondary amplification product. Because the donor and acceptor dyes flank the RERS, cleavage of the RERS results in separation of the dyes onto the separate fragments. Nicking of the RERS with displacement of the single-strand downstream of the nick results in a double-stranded fragment linked to one dye and a separate single-stranded fragment linked to the other dye. The distance between the dyes increases as the two fragments diffuse in the reaction solution, resulting in reduced quenching. A change in a fluorescence parameter resulting from reduced quenching, e.g., an increase in donor fluorescence intensity or a decrease in acceptor fluorescence intensity, may be detected and/or monitored as an indication that target amplification is occurring or has occurred.

Because cleavable or nickable secondary amplification products are produced concurrently with target amplification, the change in fluorescence may be monitored as the amplification reaction is occurring, i.e., in "real-time". Homogeneous assays reduce contamination because the reaction vessel does not have to be opened for detection and they allow the use of simpler instrumentation than in heterogeneous assays. In addition, because a change in fluorescence is monitored rather than an absolute value, the accuracy of the assay is not dependent on the starting point (i.e., establishing a "zero" point). The homogeneous, real-time assay of the invention can be used to provide semi-quantitative or quantitative information about the initial amount of target present. That is, the rate at which the selected fluorescence parameter changes during amplification is an indication of the initial target levels. As a result, when more initial copies of the target sequence are present, donor fluorescence more rapidly reaches the threshold of detection for the cleaved secondary amplification products (i.e., shorter time to positivity). The decrease in acceptor fluorescence similarly exhibits a shorter time to positivity, detected as the time required to reach a selected minimum value. In addition, the rate of change in the fluorescence parameter during the course of the reaction is more rapid in samples containing higher initial amounts of target than in samples containing lower initial amounts of amounts of target (i.e., increased slope of the curve). That is, an increased rate of change in intensity, lifetime, etc. indicates a higher initial target level than is present in a sample exhibiting a relatively slower rate of change.

In an alternative embodiment, the signal primer may be used in a non-amplification based format to detect a target oligonucleotide. In this embodiment, the target binding sequence of the signal primer hybridizes to the 3' end of the target oligonucleotide such that the RERS forms a 5' overhang. Polymerase extends the target sequence using the 5' overhang of the signal primer, including the RERS, as a template. In this case, the target sequence functions as a primer in the primer extension reaction to synthesize the complementary sequence of the signal primer. If the target binding sequence of the signal primer is complementary to the entire length of the target sequence there are no other single-stranded overhangs and only the target is extended. However, if the target binding sequence of the signal primer hybridizes to only a portion of the target sequence, the target sequence forms a second 5' overhang. In this embodiment, the signal primer is also extended using the 5' overhang of the target as a template. In either case, the RERS of the signal primer is thus rendered double-stranded and cleavable or nickable. Extension to produce the double-stranded RERS and the resulting change in fluorescence can take place only in the presence of target, and the method is independent of the presence or absence of a restriction site in the target sequence itself. As this method does not require SDA or any other amplification reaction, modified nucleotides are not necessary. Any restriction site may be employed in the signal primer. However, if the RERS is to be nicked rather than cleaved, modified nucleotides may be employed as described above to produce a singly-nickable site.

Many donor/acceptor dye pairs known in the art are useful in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), N-(4-aminobutyl)-N-ethylisoluminol (ABET)/TAMRA, and others. Near-IR dyes such as Cy5 (N, N-modified tetramethyl indodicarbocyanine) may also be employed, e.g., paired with ROX. The selection of an appropriate quenching donor/acceptor pair is routine in the art. For energy transfer quenching it is only necessary that the emission wavelengths of the donor fluorophore overlap the excitation wavelengths of the acceptor fluorophore, i.e., there must be sufficient spectral overlap between the two dyes to allow efficient energy transfer, charge transfer or fluorescence quenching. p-(Dimethyl aminophenylazo) benzoic acid (DABCYL) is a non-fluorescent acceptor dye which effectively quenches fluorescence from a neighboring fluorophore, e.g., fluorescein or 5-((2'-aminoethyl) amino) naphthalenel-sulfonic acid (EDANS). Certain donor/acceptor pairs are exemplified above and in the following Examples, however, others will be apparent to those skilled in the art and are also useful in the invention. Any dye pair which produces fluorescence quenching in the signal primers of the invention is suitable for use in the methods of the invention, regardless of the mechanism by which quenching occurs.

Terminal and internal labeling methods are also known in the art and may be used to link the donor and acceptor dyes at their respective sites in the signal primer. Examples of 5'-terminal labeling methods include a) periodate oxidation of a 5'-to-5'-coupled ribonucleotide followed by reaction with an amine-containing label, b) condensation of ethylenediamine with a 5'-phosphorylated polynucleotide followed by reaction with an amine-reactive label, and c) introduction of an aliphatic amine substituent using an aminohexyl phosphite reagent in solid-phase DNA synthesis followed by reaction with an amine-reactive label. Labels may also be linked to synthetic DNA oligonucleotides at specific locations using special aliphatic amine-containing nucleotide phosphoramidite reagents. Selection of an appropriate method for linking the selected labels to the signal primer and performing the linking reactions are routine in the art.

The signal primers of the invention have a donor and an acceptor linked to the single-stranded signal primer such that donor fluorescence is totally or partially quenched. Between the two dyes, the signal primer comprises a RERS (in single-stranded form). The two dyes must be in sufficiently close spatial proximity for quenching to occur, however, the distance between them must also allow the restriction endonuclease access to its recognition site for binding and cleavage or nicking when the signal primer is rendered double-stranded. To study the relationship of these two parameters, signal primers and their complements were chemically synthesized. The signal primer sequence selected was SEQ ID NO: 1:

5'-TAGCCT$^6$CGAGT$^{11}$AGAGT$^{16}$CTTCAAAT$^{16}$AT$^{26}$CAGAGCTTTACCTAACAA-3'

6 = nucleotide position 6

11 = nucleotide position 11

16 = nucleotide position 16

26 = nucleotide position 26

The BsoBI site for cleavage is shown bolded, with additional tail sequence 5' to it to accommodate the "footprint" of the restriction enzyme when it binds. Double-stranded cleavage of this BsoBI recognition sequence is not inhibited by incorporation of the modified deoxynucleoside triphosphates during SDA, in contrast to the CTCGGG recognition sequence for BsoBI which is rendered nickable by incorporation of modified dNTPs during SDA. The sequence 3' to the BsoBI site is the target binding sequence, which is complementary to the target sequence to be amplified. The assay was performed at 52°–53° C. in 200 $\mu$L KPDG buffer (40 mM KPi, 3% DMSO, 5% glycerol) with 5 mM Mg(OAc)$_2$ added prior to the experiment. Measurements were obtained with an SLM 8100 research grade fluorometer equipped with a circulating bath for maintaining sample compartment temperature, a xenon arc lamp and grating monochromators for controlling excitation and emission wavelengths. Experiments with fluorescein (FAM) as the donor used 488 nm for the excitation wavelength and 525 nm for emission. Experiments in which Rhodamine X (ROX) was the donor used an excitation at 580 nm and emission at 604 nm. Experiments with Cy-5 used 640 nm and 665 nm respectively. Samples were prepared with 20 nM of the labeled signal primer for initial measurements of the emission spectrum using the optimal donor excitation wavelength.

The selected donor fluorophore was conjugated to the 5' phosphate. The selected acceptor dye was conjugated to either T6, T 11, T16 or T26 to provide varying distances between the donor and acceptor dyes. Reactive dyes were obtained from Molecular Probes (Eugene, Oreg.) or from the Applied Biosystems Division of Perkin Elmer (Foster City, Calif.). ROX-NHS (6-carboxy rhodaminexsuccinimidyl ester) and TAMRA-SE (5-carboxy tetramethylrhodamine succinimidyl ester) were obtained from ABI/Perkin Elmer. Oligonucleotides were synthesized on a 1 $\mu$mole scale using an ABI 380B automated DNA synthesizer with standard reagents supplied by the manufacturer. The 6-carboxy substituted fluorescein (6-FAM) was incorporated at the 5' position by addition of the phosphoramidite reagent 6-FAM Amidite (ABI) at the final step of the synthesis. For other 5' dye labeled oligonucleotides, 5' aminohexyl phosphoramidite (ABI AMINOLINK 2) was substituted at the final step to provide a reactive amino group for subsequent conjugation. For conjugating dyes to internal positions of the oligonucleotide, a modified dT phosphoramidite reagent, amino-modifier C6 dT (Glen Research, Sterling, Va.) was substituted in the appropriate sequence position in place of unmodified dT. The crude oligonucleotides were deprotected by treatment with ammonium hydroxide for 4 to 8 hours at 55° C., which also deprotected the modified dT. These were filtered and solvent was evaporated from the filtrate with a rotary vacuum apparatus. Oligonucleotides were purified directly following this step by reverse phase HPLC. Sequences with only the modified internal dT aminolinker were prepared with the 5' terminal dimethoxytrityl (DMT) intact and purified by RP HPLC. The resulting 5'-DMT full length product was deprotected using a SepPak column (Waters) with 2% trifluoroacetic acid and dried prior to coupling with reactive dyes.

Oligonucleotides were labeled by dissolving an aliquot (0.5 μmole) in 100 μL NaHCO$_3$/Na$_2$CO$_3$ buffer, pH 8.0. The reactive dye was added to this as a solution of 3 mg in 30 μL DMSO and the resulting mixture was allowed to stand in the dark for 12–24 hours at 37° C. The resulting reaction mixture was passed over a column of G-25 Sephadex resin (NAP5, Pharmacia Biotech) eluting with 4 mM TAE (4 mM TRIS acetate, 0.1 mM EDTA, pH 8.0). Typically, the first 0.5 to 1.0 mL of colored material eluted contained the highest fraction of reactive dye-labeled oligonucleotide and was further purified by HPLC on a Waters Delta Pak 300 Å C18 3.9×150 mm reverse phase column using linear gradients over 30 minutes followed by 20 minutes re-equilibration. Most gradients used two solvents: A—98% 50 mM TEAA (triethylammonium acetate)/2% acetonitrile and B—10% 50 mM TEAA/90% acetonitrile, typically in a gradient from 95% A to 70% A over 30 minutes. The identity of the conjugated material was confirmed by comparing peak intensities at 260 nm (for DNA) and the respective peak absorbances for the dyes. Concentrations of purified oligonucleotides were determined in TAE buffer by using the DNA absorbance at 260 nm corrected for the respective dye absorbance at that wavelength.

The signal primer was initially tested for the effect of the distance between the donor and acceptor on quenching efficiency and cleavage efficiency in a hybridization assay. A 5-fold excess of the complementary sequence (100 nM) was added and the fluorescence was measured after hybridization was judged to be complete (typically about 20 min.). The BsoBI enzyme was added to a concentration of 3.2 units/μL and a final fluorescence measurement was recorded when no further change was observed in the emission spectrum of the sample. The results for the various separation distances and dye pairs are shown in Table I.

TABLE I

| Donor | Acceptor | Fluorescence | | | Ratio | |
|---|---|---|---|---|---|---|
| | | ss | ds | cleaved | ds/ss | cleaved/ss |
| ROX @ T11 | 5'-Cy5 | 3376 | 3919 | 7605 | 1.16 | 2.25 |
| 5'-FAM | ROX @ T6 | 2467 | 2973 | 3983 | 1.21 | 1.61* |
| 5'-FAM | ROX @ T11 | 3497 | 5290 | 18337 | 1.51 | 5.24 |
| 5'-FAM | ROX @ T16 | 990 | 1325 | 2007 | 1.34 | 2.03 |
| 5'-FAM | ROX @ T26 | 1900 | 1900 | 2000 | 1 | 1.1 |
| 5'-FAM | Dabcyl @ T11 | 10011 | 25566 | 45167 | 2.55 | 4.51 |
| TAMRA @ T11 | 5'-Cy5 | 7357 | 8412 | 9744 | 1.14 | 1.32 |
| 5'-ROX | ROX @ T11 | 18180 | 50080 | 46850 | 2.8 | 2.6 |
| 5'-FAM | FAM @ T11 | 4450 | 6100 | 5150 | 1.37 | 1.16 |
| 5'-Cy5 | Cy5 @ T11 | 3650 | 4150 | 4150 | 1.14 | 1.14 |

*Incomplete cleavage

These experiments show that the change in fluorescence intensity upon cleavage of the signal primer depends on the distance between the donor and acceptor fluorophores in the uncleaved signal primer. In general, as the distance between the dyes in the intact oligonucleotide increased, the change in donor emission (fluorescence intensity) upon conversion to double stranded form decreased in magnitude. The magnitude of the change in donor emission following double-stranded cleavage also generally decreased with increasing distance between the dyes. Dye pairs which too closely flanked the RERS appeared to interfere with complete cleavage, also reducing the total change in donor fluorescence. Signal primers with about eleven nucleotides between the donor and acceptor typically exhibited the greatest change in donor fluorescence upon conversion to double-stranded form and cleavage of the RERS. These results indicate, however, that about 8–20 nucleotide separation, preferably about 10–16 nucleotides between the donor and acceptor dyes produces a change in donor fluorescence of a readily detectable magnitude. These separation distances are also sufficient to accommodate binding of the restriction endonouclease to its recognition site without significant interference from the bulky dyes, while still placing the dyes in sufficiently close proximity to produce satisfactory quenching. Greater changes in donor fluorescence would be expected if the two dyes could be brought into closer proximity on the signal primer, however, placing the acceptor closer to the donor than six nucleotides interfered with the ability of the restriction enzyme to cleave the duplex, although an increase in donor fluorescence was still detectable. This demonstrates that even a small amount of signal primer conversion results in a relatively large change in fluorescence.

An increase in donor fluorescence was usually observed upon conversion to double-stranded form alone. This is likely to be due to a reduction in quenching occurring by mechanisms other than Förster transfer which may take place in the single-stranded oligonucleotide (e.g., charge transfer, collisional quenching). Target amplification may therefore be detected by monitoring only the change in fluorescence upon conversion of the signal primer to double-stranded form. In this case an RERS in the signal primer is not necessary. In most cases, however, cleavage further increased the change in fluorescence. Monitoring the total change in fluorescence (double-stranded conversion and cleavage or nicking) is preferred for this reason. Regardless of the magnitude of the fluorescence change at each step of the process (i.e., single-stranded to double-stranded conversion, and conversion of the double-stranded form to the cleaved or nicked form) a readily detectable increase in donor fluorescence was evidenced by a cut/ss ratio significantly greater than 1 when the dye pair was sufficiently far apart for efficient cleavage but in sufficiently close proximity to optimize quenching. In an end-point assay a larger change in fluorescence may be detectable if end-point fluorescence is monitored at a lower temperature than initial fluorescence. When the change in fluorescence is monitored in real-time, its magnitude will be affected by the temperature of the reaction. At higher temperatures the change in fluorescence associated with double-stranded conversion and cleavage is generally smaller than at lower temperatures.

It was also observed that homologous donor/acceptor dye pairs (shown in the last three lines of the Table) exhibited an increase in donor fluorescence intensity only upon conversion from single- to double-stranded form. In contrast to heterologous dye pairs, no further increase was obtained upon cleavage of the double-stranded oligonuceotide, and in some cases cleavage produced a slight reduction in donor fluorescence intensity. Therefore, signal primers employing these fluorophore pairs need not contain an RERS. Target may be detected using the ss/ds ratio or a change in fluorescence associated with the conversion to double-stranded form, as quenching of the fluorophores decreases (i.e., fluorescence intensity will increase) as the signal primer is converted to double-stranded form in the presence of target.

It will be apparent that, in addition to SDA, the methods of the invention may be easily adapted to other primer extension amplification methods (e.g., PCR, 3SR, NASBA, TMA, etc.). For example, replacing SDA amplification primers with PCR amplification primers and using a PCR DNA polymerase which lacks 5'→3' exonuclease activity (e.g., Sequencing Grade Taq from Promega or exo⁻ Vent or exo⁻ Deep Vent from New England BioLabs) in the signal primer reaction scheme also generates secondary amplification products which contain a cleavable, double-stranded RERS contributed by the signal primer. Of course, in PCR any RERS may be selected for use in the signal primer, as there are typically no modified deoxynucleoside triphosphates present which might induce nicking rather than cleavage of the RERS. The double-stranded RERS in the secondary amplification product may be cleaved by a restriction endonuclease to separate a donor/acceptor dye pair as described above. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, cleavage of the REKS and separation of the dye pair reduces fluorescence quenching, with the increase in fluorescence intensity serving as an indication of target amplification.

For adaptation of the inventive methods to 3SR, NASBA or TMA, a 5'→3' exonuclease deficient reverse transcriptase with strand displacing activity is employed in the 3SR reaction, with hybridization of the signal primer to the RNA target downstream of an amplification primer which contains an RNA polymerase promoter. In a reaction scheme similar to that previously described, the hybridized signal primer containing the RERS is 1) extended, and 2) displaced by extension of the upstream amplification primer. The displaced extension product is then made double-stranded by hybridization and extension of the second amplification primer. This renders the restriction endonuclease recognition site cleavable, and the donor and acceptor dyes are thereby separated onto different fragments, increasing the distance between them and reducing fluorescence quenching of the donor dye. The signal primer for 3SR or NASBA does not contain an RNA polymerase promoter sequence and therefore cannot function as an amplification primer, reducing nonspecific background signal. This is analogous to the signal primer in SDA, which does not contain a repeatably nickable RERS and therefore does not contribute to exponential background amplification of non-specific targets.

For reasons previously stated, signal primers are preferred for use in the methods of the invention with the signal primer extension product being separated from the target sequence by displacement due to extension of the upstream amplification primer. However, it will be apparent that the amplification primers known for use in the various nucleic acid amplification reactions may also be labeled and modified as described for signal primers. In this embodiment, the labeled amplification primer extension product may be separated from the target sequence by displacement due to extension of an upstream non-amplification primer (e.g., bumper primers as in SDA), by denaturation (e.g., heating as in PCR) or by enzymatic digestion of the target strand (e.g., RNase H as in 3SR). Amplification primers comprising the RERS flanked by the donor/acceptor dye pair eliminate the need for the additional signal primer in the reaction, but because background may be higher in this embodiment the sensitivity of the assay may be decreased. For PCR, the amplification primer is modified by addition of an RERS in a 5' tail and the RERS is flanked by a donor/acceptor dye pair. This primer is structurally identical to the PCR signal primer described above. Functionally, however, it is different in that there is no downstream primer to be extended and displaced and the amplification primer itself provides the change in fluorescence. For 3SR, NASBA and TMA, the RERS may be placed 5' to the promoter of an amplification primer so that the RERS is cleaved in the double-stranded DNA portion of the amplification cycle. Because the RERS is 5' to the promoter, cleavage does not remove the promoter from the amplification primer and generation of RNA transcripts continues to sustain target amplification. A second amplification primer which does not contain a promoter sequence (e.g., as in NASBA) may also or alternatively contain the RERS in a 5' tail portion.

Target DNA for the following experimental examples was prepared from stocks of Chlamydia trachomatis elementary bodies (EB's) stored at concentrations of $10^6$ EB's/$\mu$L in 50% glycerol. EB stock solutions were diluted 1:10 in water, boiled for 15 minutes and prepared as 10-fold serial dilutions in 10 ng/$\mu$L human placental DNA. These stock solutions contained 1 to 100 genome copies/$\mu$L of target. The donor fluorophore was conjugated to the 5' phosphate. Measurements were obtained with an SLM 8100 research grade fluorometer equipped with a circulating bath for maintaining sample compartment temperature, a xenon arc lamp and grating monochromators for controlling excitation and emission wavelengths. Experiments with fluorescein (FAM) as the donor used 488 nm for the excitation wavelength and 525 nm for emission. Experiments in which ROX was the donor used an excitation at 580 nm and emission at 604 nm.

EXAMPLE 1

SDA was performed generally as described in EP 0 684 315, with addition of the signal primer labeled at the 5' end with FAM and at T11 with ROX. The final concentrations of components in each 100 $\mu$L reaction were 40 mM K$_i$PO4 pH 7.5, 6 mM MgOAc, 0.2 mM each dTTP, dGTP, dATP, 1.4 mM dCTP$\alpha$S, 20 $\mu$g/mL acetylated BSA, 3% DMSO, 8% (v/v) glycerol, 100 ng human placental DNA, 25 units Bst polymerase (exo⁻ klenow fragment, New England BioLabs), 150 units AvaI (New England BioLabs, Beverly, Mass.), and DNA from 0, 10, 100 or 1,000 Chlamydia trachomatis elementary bodies. Each sample further contained 50 nM signal primer SEQ ID NO: 1 (5'-FAM/T$^{11}$-ROX) and the four primers shown below:

Amplification primer S1.1 (SEQ ID NO:2, 750 nM)
  ACCGCATCGAATCGATGTCTCGGGTA-GAAAATCGCATGCAAGATA
Amplification primer S2.1 (SEQ ID NO:3, 188 nM)
  CGATTCCGCTCCAGACTTCTCGGGAGCT-GCCTCAGAATATACTCAG
Bumper primer B1 (SEQ ID NO:4, 75 nM)
  TAAACATGAAAACTCGTTCCG
Bumper primer B2 (SEQ ID NO:5, 75 nM)
  TTTTATGATGAGAACACTTAAACTCA Each reaction was assembled to contain all reagents except Bst and AvaI, and the samples were then heated for 2 min. at 95° C. They were transferred to a 53.5° C. water bath for 3–5 min. and the enzymes were added for a total sample volume of 100 $\mu$L. The samples were then transferred to 225 μL cuvettes and placed into a research grade SLM 8100 spectrofluorometer (Spectronic Instruments, Rochester, N.Y.). The temperature of the cuvettes was maintained at 53°–54° C. by a circulating water bath, and the fluorescence emission of each cuvette at 520 nm ($\lambda_{excitation}$= 488 nm) was recorded every 8 sec. Reactions were typically followed for 60–90 min.

Figure 2:
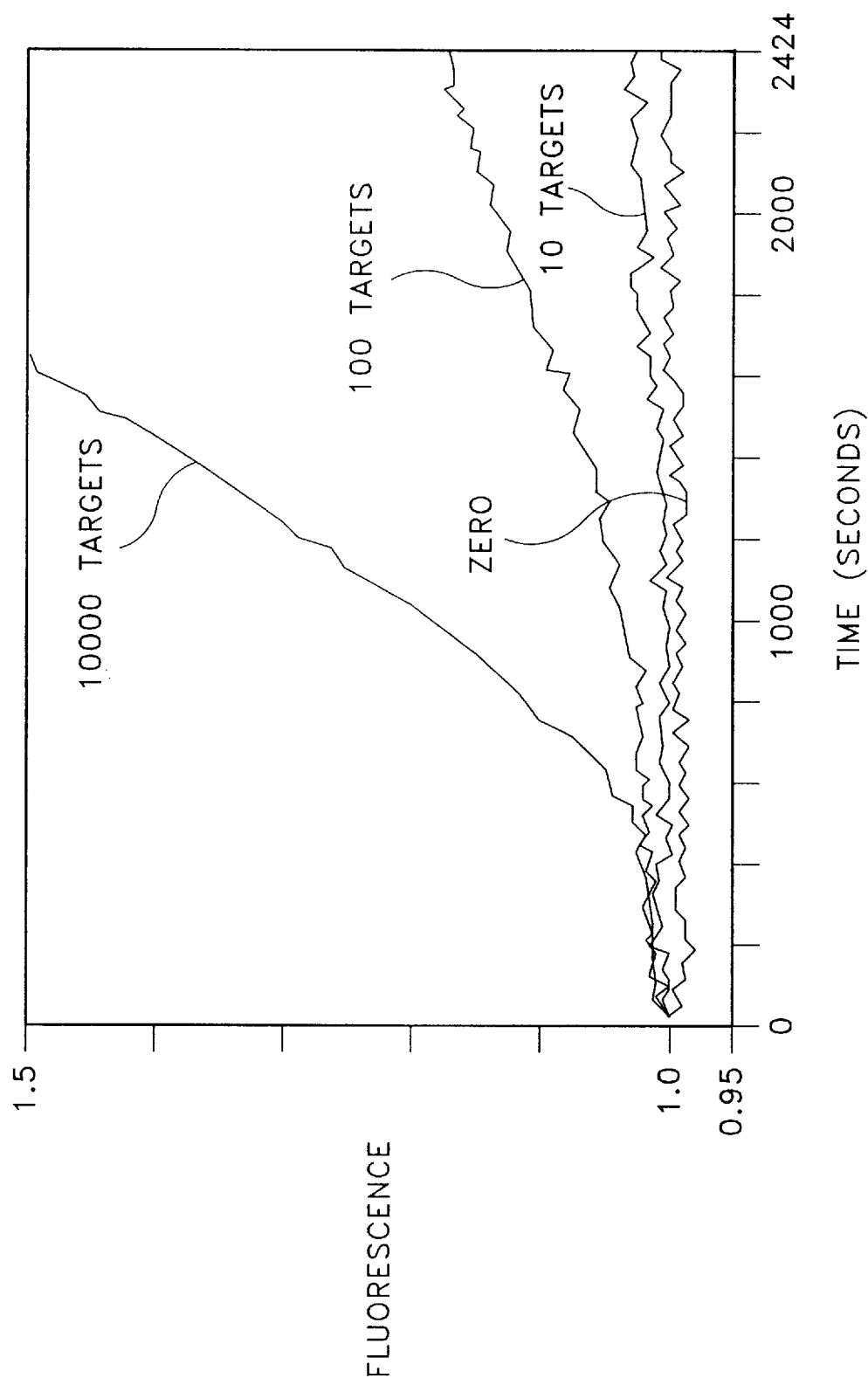
FIG. 2 shows the change in fluorescence intensity which occurs as a nucleic acid target is amplified using the signal primers of the invention.

FIG. 2 shows the results. Fluorescence remained low (quenched) in the control reaction containing no target (no amplification) but increased significantly in reactions containing 100 and 1,000 targets, demonstrating specific detection of target amplification. There was no appreciable increase in fluorescence in the reaction containing 10 targets, indicating a sensitivity of detection between 10 and 100 targets. In addition, the rate of increase in fluorescence intensity of the donor (a measure of the rate of decrease in donor quenching) was more rapid in samples containing higher numbers of initial target. The rate of increase in donor fluorescence therefore provides not only detection of amplification in real-time, but also a semi-quantitative or relative measure of initial target levels. By comparing the rate of increase in fluorescence in a sample containing an unknown amount of target to the increase in fluorescence in a series of reactions containing varying known amounts of target (producing a standard curve as is known in the art) a quantitative measure of target levels in the unknown sample may be obtained. Alternatively, detection of an increase in fluorescence intensity above a predetermined threshold value may be used as an indication that the target is present and amplified in a simple positive/negative assay format.

EXAMPLE 2

A signal primer according to the invention was used to detect a target oligonucleotide in the absence of target amplification. An unlabeled target oligonucleotide having the following sequence was synthesized by conventional methods:

TTGTTAGGTAAAGCTCTGATATTTGAAG (SEQ ID NO:6)

This target is complementary to the 3' target binding sequence of signal primer SEQ ID NO: 1.

Four glass cuvettes (225 μL, Starna Cells) were each filled with 100 μL of a solution comprising 50 nM signal primer, 5 mM Mg(OAc)$_2$, 0.2 mM each deoxynucleotide triphosphate, 1.4 mM α-thio dCTP, 40 mM potassium phosphate (pH 7.5), 3% DMSO (v/v), and 5% glycerol. SEQ ID NO:6 was added to each cuvette to a final concentration of 0, 2.5, 25 or 250 nM representing 0. 0.05, 0.5 and 5 molar equivalents of target per equivalent of signal primer. The samples were then heated briefly to 95° C. and cooled to 54° C. in an SLM 8100 fluorometer. Bst polymerase (180 units) and BsoBI (240 units) were added to each cuvette and the fluorescence intensity was recorded at 520 nm ($\lambda_{excitation}$= 488 nm) as described in Example 1.

The results are shown in FIG. 3. Fluorescence did not change in the absence of target, but increased over the course of the hybridization, extension and cleavage reaction in all samples containing target. The magnitude of the change in fluorescence intensity increased in approximate proportion to the amount of target. Further, the rate of change in fluorescence intensity was greater as the amount of target increased. Either of these parameters may be used as a means for quantitating target levels, typically by comparison to the results obtained for known amounts of target used as standards.

What is claimed is:

1. A method for detecting presence of a target sequence comprising:
    a) hybridizing to the target sequence a signal primer comprising a target binding sequence and a single-stranded restriction endonuclease recognition sequence 5' to the target binding sequence, the restriction endonuclease recognition sequence flanked by a donor fluorophore and an acceptor dye such that fluorescence of the donor fluorophore is quenched;
    b) in a primer extension reaction, synthesizing a complementary strand using the signal primer as a template, thereby rendering the restriction endonuclease recognition sequence double-stranded;
    c) cleaving or nicking the double-stranded restriction endonuclease recognition sequence with a restriction endonuclease, thereby reducing donor fluorophore quenching and producing a change in a fluorescence parameter, and;
    d) detecting the change in the fluorescence parameter as an indication of the presence of the target sequence.

2. The method of claim 1 wherein the complementary strand is synthesized in a target amplification reaction.

3. The method of claim 1 wherein the complementary strand is synthesized by extension of the target sequence using the signal primer as a template.

4. The method of claim 1 wherein a change in fluorescence intensity is detected as an indication of the presence of the target sequence.

5. The method of claim 4 wherein an increase in donor fluorophore fluorescence intensity or a decrease in acceptor dye fluorescence intensity is detected as an indication of the presence of the target sequence.

6. The method of claim 5 wherein the change in fluorescence intensity is detected as i) an increase in a ratio of donor fluorophore fluorescence after cleaving or nicking to donor fluorophore fluorescence in the signal primer, or ii) as a decrease in a ratio of acceptor dye fluorescence after cleaving or nicking to acceptor dye fluorescence in the signal primer.

7. The method of claim 1 wherein a change in fluorescence lifetime of the donor fluorophore or the acceptor dye is detected as an indication of the presence of the target sequence.

8. The method of claim 1 wherein the change in the fluorescence parameter is detected in real-time.

9. The method of claim 1 wherein the change in the fluorescence parameter is detected at an endpoint.

10. The method of claim 1 wherein the donor fluorophore and the acceptor dye are separated by about 8–20 nucleotides in the signal primer.

11. The method of claim 10 wherein the donor fluorophore and the acceptor dye are separated by about 10–16 nucleotides in the signal primer.

12. The method of claim 1 wherein the donor fluorophore is fluorescein and the acceptor dye is Rhodamine X.

13. A method for detecting amplification of a target sequence comprising, in an amplification reaction:
   a) hybridizing to the target sequence a first primer comprising a target binding sequence and a restriction endonuclease recognition sequence 5' to the target binding sequence, the restriction endonuclease recognition sequence flanked by a donor fluorophore and an acceptor dye such that fluorescence of the donor fluorophore is quenched;
   b) extending the hybridized first primer on the target sequence with a polymerase to produce a first primer extension product and separating the first primer extension product from the target sequence;
   c) rendering the separated first primer extension product and the restriction endonuclease recognition sequence double-stranded by hybridization and extension of a second primer;
   d) cleaving or nicking the double-stranded restriction endonuclease recognition sequence with a restriction endonuclease, thereby reducing donor fluorophore quenching and producing a change in a fluorescence parameter, and;
   e) detecting the change in the fluorescence parameter as an indication of amplification of the target sequence.

14. The method of claim 13 wherein the target sequence is amplified by Strand Displacement Amplification.

15. The method of claim 14 further comprising nicking of the double-stranded restriction endonuclease recognition sequence in an amplification primer during target amplification.

16. The method of claim 15 wherein the restriction endonuclease is BsoBI or AvaI.

17. The method of claim 14 further comprising a second restriction endonuclease which nicks a second double-stranded restriction endonuclease recognition sequence in an amplification primer during target amplification.

18. The method of claim 13 wherein the target sequence is amplified by the Polymerase Chain Reaction, 3SR, TMA or NASBA.

19. The method of claim 13 wherein the first primer is a signal primer.

20. The method of claim 19 wherein the second primer is an amplification primer.

21. The method of claim 13 wherein the first and second primers are amplification primers.

22. The method of claim 13 wherein the change in the fluorescence parameter is detected in real-time.

23. The method of claim 13 wherein the change in the fluorescence parameter is detected at a selected end-point in the amplification reaction.

24. The method of claim 13 wherein the donor fluorophore and the acceptor dye are separated by about 8–20 nucleotides in the first primer.

25. The method of claim 24 wherein the donor fluorophore and the acceptor dye are separated by about 10–16 nucleotides in the first primer.

26. The method of claim 13 wherein the donor fluorophore is fluorescein and the acceptor dye is Rhodamine X.

27. The method of claim 26 wherein the donor fluorophore and the acceptor dye are separated by 11 nucleotides in the first primer.

28. The method of claim 13 wherein the donor fluorophore is fluorescein and the acceptor dye is DABCYL.

29. The method of claim 28 wherein the donor fluorophore and the acceptor dye are separated by 11 nucleotides in the first primer.

30. The method of claim 13 wherein the donor fluorophore is Rhodamine X and the acceptor dye is Cy5.

31. The method of claim 30 wherein the donor fluorophore and the acceptor dye are separated by 11 nucleotides in the first primer.

32. The method of claim 13 wherein a change in donor fluorophore or acceptor dye fluorescence intensity is detected as an indication of amplification of the target sequence.

33. The method of claim 32 wherein the change in the fluorescence intensity is detected i) as an increase in a ratio of donor fluorophore fluorescence after cleaving or nicking to donor fluorophore fluorescence in the first primer, or ii) as a decrease in a ratio of acceptor dye fluorescence after cleaving or nicking to acceptor dye fluorescence in the first primer.

34. A method for detecting amplification of a target sequence comprising, in an amplification reaction:
   a) hybridizing to the target sequence a first primer comprising a donor fluorophore and an acceptor dye, the donor fluorophore and the acceptor dye linked to the first primer such that fluorescence of the donor fluorophore is quenched;
   b) extending the hybridized first primer on the target sequence with a polymerase to produce a first primer extension product and separating the first primer extension product from the target sequence;
   c) rendering the separated first primer extension product double-stranded by hybridization and extension of a second primer, thereby reducing donor fluorophore quenching and producing a change in a fluorescence parameter and;
   d) detecting the change in the fluorescence parameter as an indication of amplification of the target sequence.

35. The method of claim 34 wherein the donor fluorophore and the acceptor dye are an homologous dye pair.

36. The method of claim 35 wherein a change in donor fluorophore or acceptor dye fluorescence intensity is detected as an indication of amplification of the target sequence.

37. The method of claim 36 wherein the change in fluorescence intensity is detected i) as an increase in a ratio of donor fluorophore fluorescence in the double-stranded first primer extension product to donor fluorophore fluorescence in the first primer, or ii) as a decrease in a ratio of acceptor dye fluorescence in the double-stranded first primer extension product to acceptor dye fluorescence in the first primer.

38. The method of claim 35 wherein the donor fluorophore and the acceptor dye are selected from the group consisting of Cy5, Rhodamine X and fluorescein.

39. The method of claim 38 wherein the donor fluorophore and the acceptor dye are Rhodamine X.

40. The method of claim 34 wherein the donor fluorophore and the acceptor dye are a heterologous dye pair.

41. The method of claim 40 wherein a change in donor fluorophore or acceptor dye fluorescence intensity is detected as an indication of amplification of the target sequence.

42. The method of claim 41 wherein the change in fluorescence intensity is detected i) as an increase in a ratio of donor fluorophore fluorescence in the double-stranded first primer extension product to donor fluorophore fluorescence in the first primer, or ii) as a decrease in a ratio of acceptor dye fluorescence in the double-stranded first primer extension product to acceptor dye fluorescence in the first primer.

43. The method of claim 40 wherein the donor fluorophore is fluorescein and the acceptor dye is Rhodamine X or DABCYL.

44. The method of claim 34 wherein the first primer is a signal primer.

45. The method of claim 44 wherein the second primer is an amplification primer.

46. The method of claim 34 wherein the first and second primers are amplification primers.

47. A single-stranded oligonucleotide comprising:
(a) a target binding sequence;
(b) a restriction endonuclease recognition site 5' to the target binding sequence, and;
(c) a first dye and a second dye linked to the oligonucleotide at positions flanking the restriction endonuclease recognition site such that fluorescence of the first or the second dye is quenched.

48. The oligonucleotide of claim 47 wherein the first and second dyes are about 8–20 nucleotides apart in the oligonucleotide.

49. The oligonucleotide of claim 48 wherein the first and second dyes are about 10–16 nucleotides apart in the oligonucleotide.

50. The oligonucleotide of claim 49 wherein the first and second dyes are 11 nucleotides apart in the oligonucleotide.

51. The oligonucleotide of claim 47 wherein the first dye is fluorescein and the second dye is Rhodamine X or DABCYL.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 44 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:1:

TAGCCTCGAG TAGAGTCTTC AAATATCAGA GCTTTACCTA ACAA    4 4

( 2 ) INFORMATION FOR SEQ ID NO:2:

( i ) SEQUENCE CHARACTERISTICS:
        ( A ) LENGTH: 45 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

ACCGCATCGA ATCGATGTCT CGGGTAGAAA ATCGCATGCA AGATA    4 5

( 2 ) INFORMATION FOR SEQ ID NO:3:

( i ) SEQUENCE CHARACTERISTICS:
    ( A ) LENGTH: 46 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:3:

CGATTCCGCT CCAGACTTCT CGGGAGCTGC CTCAGAATAT ACTCAG    46

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TAAACATGAA AACTCGTTCC G    21

( 2 ) INFORMATION FOR SEQ ID NO:5:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TTTTATGATG AGAACACTTA AACTCA    26

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TTGTTAGGTA AAGCTCTGAT ATTTGAAG    28